(12) United States Patent
Ichihara et al.

(10) Patent No.: US 10,285,604 B2
(45) Date of Patent: May 14, 2019

(54) MEDICAL IMAGE DIAGNOSTIC APPARATUS, MEDICAL IMAGE PROCESSING APPARATUS, AND MEDICAL IMAGE PROCESSING METHOD

(71) Applicants: Fujita Health University, Toyoake-shi (JP); Toshiba Medical Systems Corporation, Otawara-shi (JP)

(72) Inventors: Takashi Ichihara, Nagoya (JP); Takuya Sakaguchi, Utsunomiya (JP)

(73) Assignees: Fujita Health University, Toyoake-shi (JP); Toshiba Medical Systems Corporation, Otawara-shi (JP)

( * ) Notice: Subject to any disclaimer, the term of this patent is extended or adjusted under 35 U.S.C. 154(b) by 1000 days.

(21) Appl. No.: 14/453,665

(22) Filed: Aug. 7, 2014

(65) Prior Publication Data
US 2014/0350393 A1    Nov. 27, 2014

Related U.S. Application Data

(63) Continuation of application No. PCT/JP2013/078601, filed on Oct. 22, 2013.

(30) Foreign Application Priority Data

Oct. 22, 2012  (JP) .............................. 2012-233142
Oct. 21, 2013  (JP) .............................. 2013-218751

(51) Int. Cl.
    *A61B 6/00*       (2006.01)
    *A61B 5/0295*     (2006.01)
    (Continued)

(52) U.S. Cl.
    CPC ............ *A61B 5/0295* (2013.01); *A61B 5/029* (2013.01); *A61B 6/03* (2013.01); *A61B 6/463* (2013.01);
    (Continued)

(58) Field of Classification Search
    None
    See application file for complete search history.

(56) References Cited

U.S. PATENT DOCUMENTS 7,496,175 B2 *  2/2009  Sakaguchi ........... A61B 6/4233
                                                  378/95
8,315,812 B2    11/2012  Taylor
                (Continued)

FOREIGN PATENT DOCUMENTS

CN      1600268 A       3/2005
CN    102596042 A       7/2012
                (Continued)

OTHER PUBLICATIONS

Office Action and Search Report dated Jul. 24, 2015 in the corresponding Chinese Patent Application No. 201380003596.4.
(Continued)

*Primary Examiner* — Jonathan Cwern
(74) *Attorney, Agent, or Firm* — Oblon, McClelland, Maier & Neustadt, L.L.P.

(57) ABSTRACT

According to one embodiment, a medical image diagnostic apparatus includes a storage unit, a blood flow information generation unit and a blood flow inhibition index generation unit. The storage unit stores volume data or data of a series of images regarding an organ of an object. The blood flow information generation unit generates, based on the volume data or the data of the series of images, first blood flow information of a first region and second blood flow information of a second region different from the first region. The blood flow inhibition index generation unit generates, based on the first blood flow information and the second blood flow information, a blood flow inhibition index representing a degree of inhibition of a blood flow in a blood vessel regarding the first region or the second region.

7 Claims, 9 Drawing Sheets

(51) Int. Cl.
*G06T 7/00* (2017.01)
*A61B 5/029* (2006.01)
*A61B 6/03* (2006.01)

(52) U.S. Cl.
CPC .............. *A61B 6/469* (2013.01); *A61B 6/481* (2013.01); *A61B 6/503* (2013.01); *A61B 6/504* (2013.01); *A61B 6/507* (2013.01); *A61B 6/5217* (2013.01); *G06T 7/0012* (2013.01); *A61B 6/032* (2013.01); *A61B 6/4441* (2013.01); *G06T 2207/30104* (2013.01)

(56) References Cited

U.S. PATENT DOCUMENTS

| | | | |
|---|---|---|---|
| 8,548,778 B1* | 10/2013 | Hart | G06T 19/20 600/416 |
| 2005/0065432 A1 | 3/2005 | Kimura | |
| 2010/0094118 A1* | 4/2010 | Kobayashi | A61B 5/026 600/410 |
| 2010/0289813 A1 | 11/2010 | Nobe et al. | |
| 2012/0041739 A1* | 2/2012 | Taylor | A61B 5/02007 703/11 |
| 2012/0072190 A1* | 3/2012 | Sharma | A61B 5/026 703/2 |
| 2012/0099775 A1* | 4/2012 | Rao | G06T 7/0012 382/131 |
| 2012/0190967 A1 | 7/2012 | Nahm | |
| 2012/0243761 A1* | 9/2012 | Senzig | G06T 11/008 382/131 |
| 2012/0307961 A1 | 12/2012 | Ikeda | |
| 2012/0321153 A1* | 12/2012 | Dwivedi | A61B 6/469 382/128 |
| 2013/0172734 A1* | 7/2013 | Hsieh | A61B 6/032 600/425 |
| 2013/0226003 A1* | 8/2013 | Edic | A61B 5/026 600/454 |
| 2013/0243301 A1 | 9/2013 | Sakaguchi et al. | |
| 2014/0086461 A1* | 3/2014 | Yao | A61B 6/032 382/128 |
| 2014/0114618 A1* | 4/2014 | Fonte | G06T 19/00 703/1 |

FOREIGN PATENT DOCUMENTS

| | | |
|---|---|---|
| JP | 2008-136800 A | 6/2008 |
| JP | 2010-5456 A | 1/2010 |
| JP | 2010-286472 A | 12/2010 |
| JP | 2012-90772 A | 5/2012 |
| JP | 2012-161593 A | 8/2012 |

OTHER PUBLICATIONS

U.S. Appl. No. 13/886,910, filed May 3, 2013, 2013-0243301, Sakaguchi, et al.
International Search Report dated Jan. 28, 2014 for PCT/JP2013/078601 filed on Oct. 22, 2013 with English Translation.
International Written Opinion dated Jan. 28, 2014 for PCT/JP2013/078601 filed on Oct. 22, 2013.

\* cited by examiner

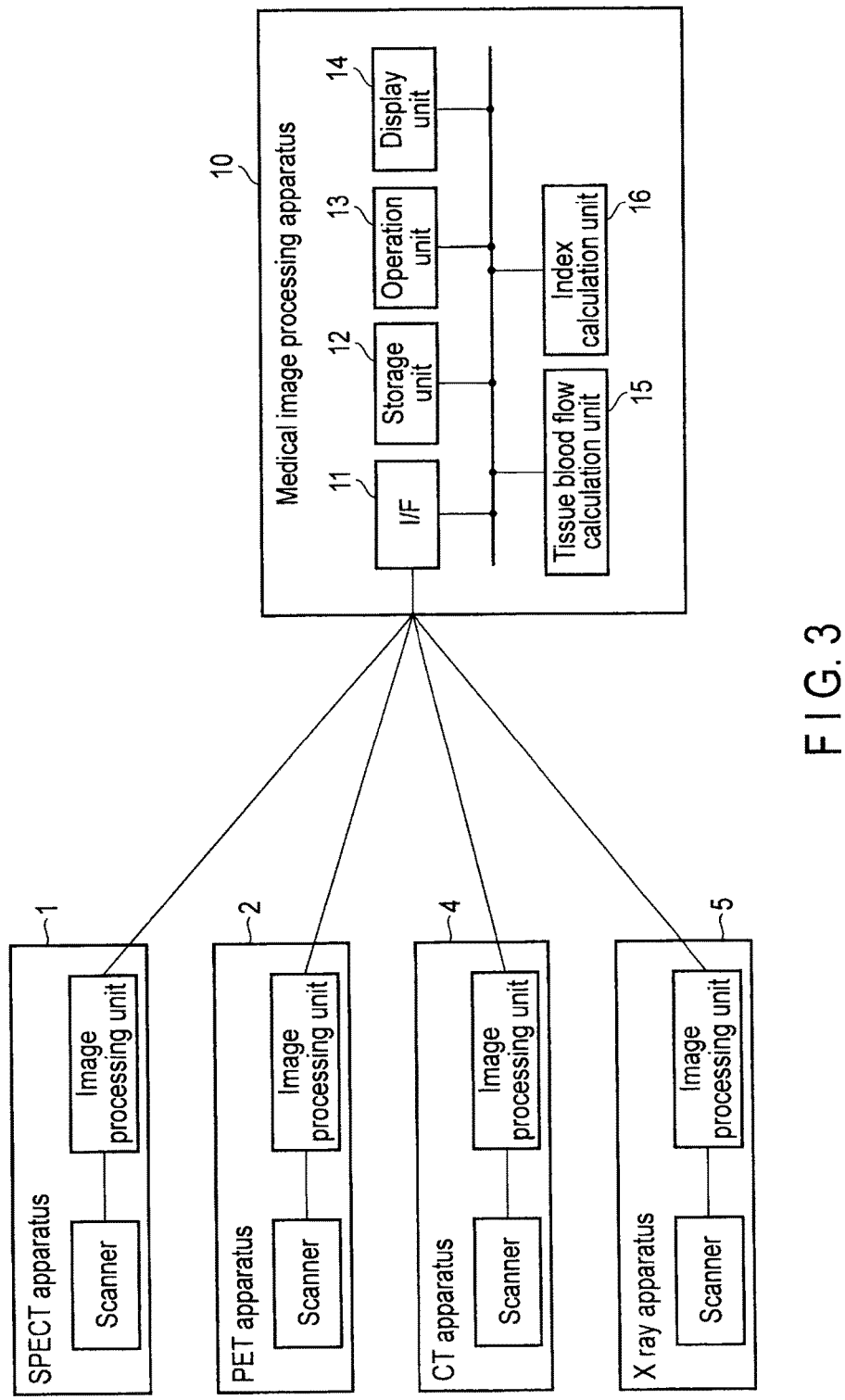
F I G. 3

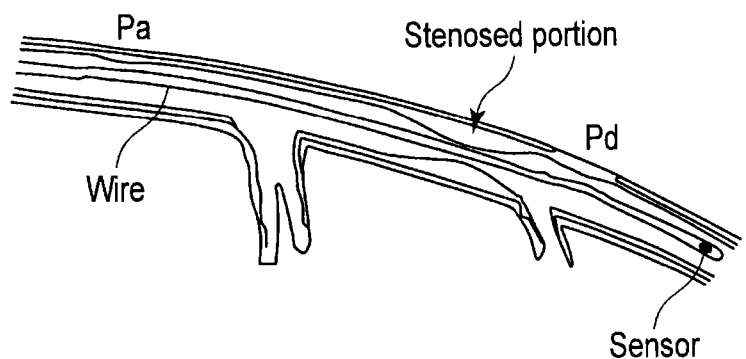
F I G. 6

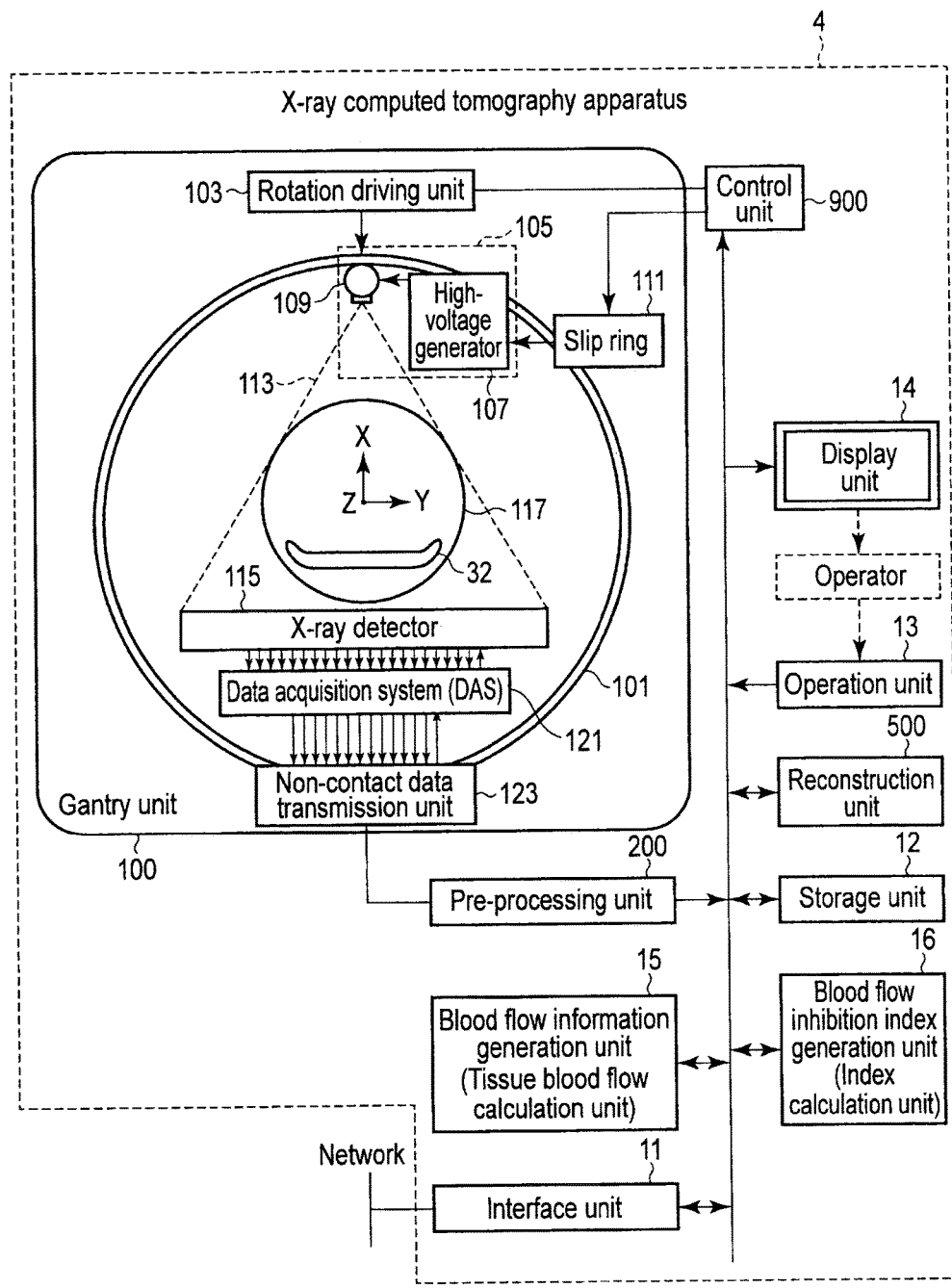
F I G. 10

MEDICAL IMAGE DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application is a Continuation application of PCT Application No. PCT/JP2013/078601, filed Oct. 22, 2013 and based upon and claiming the benefit of priority from the Japanese Patent Application No. 2012-233142, filed Oct. 22, 2012 and the Japanese Patent Application No. 2013-218751, filed Oct. 21, 2013, the entire contents of all of which are incorporated herein by reference.

FIELD

Embodiments described herein relate generally to a medical image diagnostic apparatus, medical image processing apparatus, and medical image processing method.

BACKGROUND

As a method of checking whether the cause of ischemia of a patient suffering ischemic heart disease is a stenosis, a method using a fractional flow reserve (FFR) index has been developed. The clinical effectiveness of FFR has been confirmed by randomized clinical trials.

To obtain FFR, it is necessary to insert a pressure sensor-equipped wire (pressure wire) into a blood vessel and measure a stenosed blood vessel upstream pressure Pa and stenosed blood vessel downstream pressure Pd, as shown in FIG. 6.

BRIEF DESCRIPTION OF THE DRAWINGS

FIG. 3 is a block diagram showing the arrangement of a medical image processing apparatus according to the embodiment.

FIG. 6 is a view for explaining conventional FFR.

FIG. 10 is a view showing the arrangement of an X-ray computed tomography apparatus according to a medical image diagnostic apparatus of an embodiment.

DETAILED DESCRIPTION

A medical image diagnostic apparatus according to embodiment includes a storage unit, a blood flow information generation unit, and a blood flow inhibition index generation unit.

The storage unit stores volume data or data of a series of images regarding an organ of an object. The blood flow information generation unit generates, based on the volume data or the data of the series of images, first blood flow information of a first region and second blood flow information of a second region different from the first region. The blood flow inhibition index generation unit generates, based on the first blood flow information and the second blood flow information, a blood flow inhibition index representing a degree of inhibition of a blood flow in a blood vessel regarding the first region or the second region.

A medical image diagnostic apparatus and medical image processing apparatus according to an embodiment will now be described with reference to the accompanying drawings.

(First Embodiment)

Figure 7:
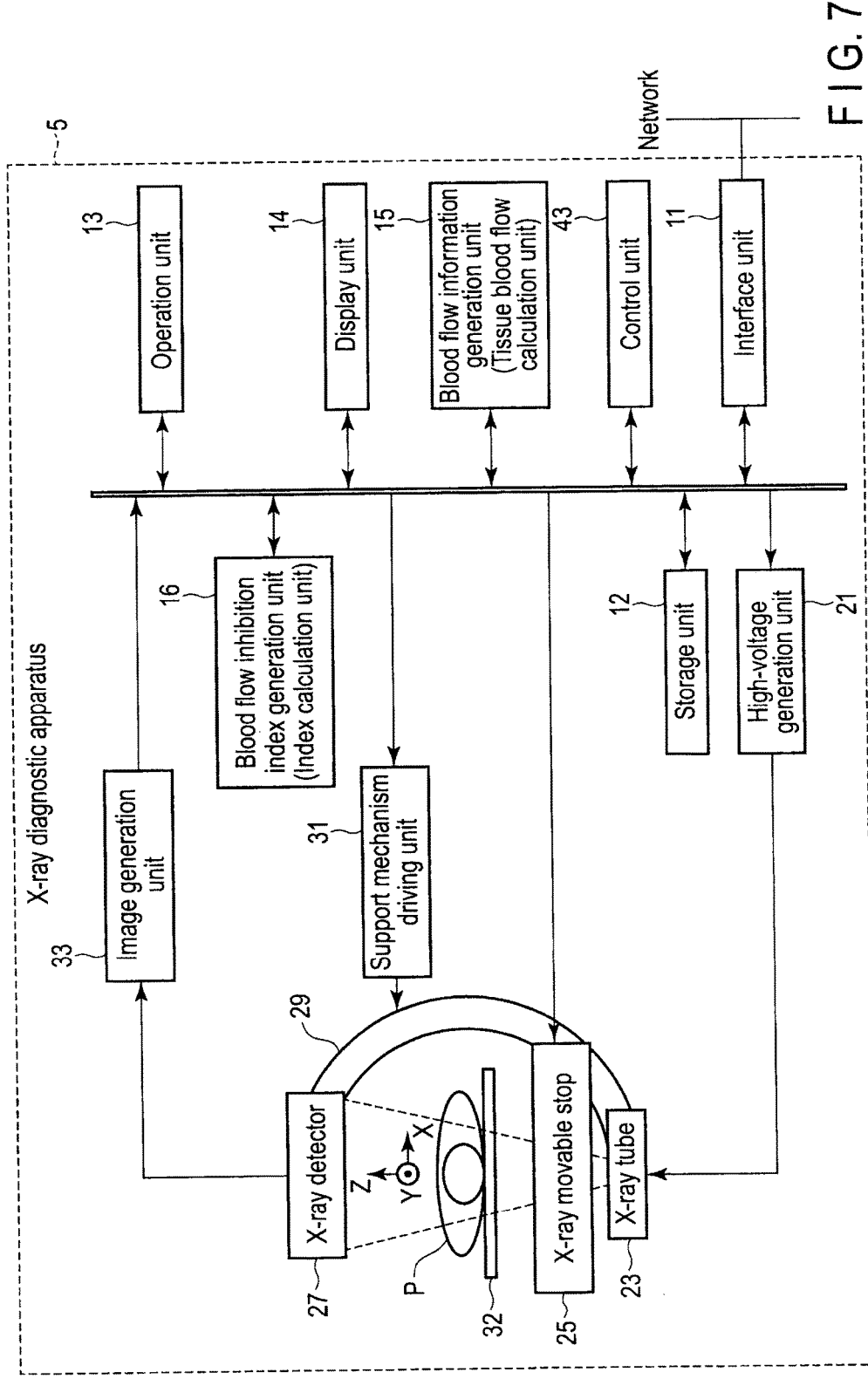
FIG. 7 is a view showing the arrangement of an X-ray diagnostic apparatus according to a medical image diagnostic apparatus of the embodiment.

FIG. 7 is a view showing an example of the arrangement of an X-ray diagnostic apparatus 5 according to a medical image diagnostic apparatus of the first embodiment. The X-ray diagnostic apparatus 5 includes a high-voltage generation unit 21, X-ray tube 23, X-ray movable stop 25, X-ray detector 27, support mechanism 29, support mechanism driving unit 31, top 32, image generation unit 33, interface (to be referred to as an I/F hereinafter) unit 11, storage unit 12, display unit 14, operation unit 13, control unit 43, blood flow information generation unit 15 (tissue blood flow calculation unit), and blood flow inhibition index generation unit (index calculation unit) 16.

The high-voltage generation unit 21 generates a tube current to be supplied to the X-ray tube 23 (to be described later) and a tube voltage to be applied to the X-ray tube 23. The high-voltage generation unit 21 supplies, to the X-ray tube 23, a tube current suited to X-ray imaging and applies, to the X-ray tube 23, a tube voltage suited to X-ray imaging. More specifically, the high-voltage generation unit 21 generates a tube voltage and tube current complying with X-ray imaging conditions under the control of the control unit 43 (to be described later).

The X-ray tube 23 generates X-rays from an X-ray focus (to be referred to as a tube focus hereinafter) based on the tube current supplied from the high-voltage generation unit 21 and the tube voltage applied from the high-voltage generation unit 21. The generated X-rays are radiated from an X-ray radiation window in the X-ray tube 23. An axis which passes through the tube focus and is perpendicular to the X-ray detection surface of the X-ray detector 27 (to be described later) is defined as the z-axis. A direction (to be referred to as the first direction hereinafter) perpendicular to the z-axis and parallel to the major axis direction of the top 32 (to be described later) is defined as the x-axis. An axis (direction parallel to the minor axis direction of the top 32: to be referred to as the second direction hereinafter) perpendicular to the z- and x-axes is defined as the y-axis.

The X-ray movable stop 25 includes a plurality of aperture blades (not shown). The X-ray movable stop 25 is arranged in front of the X-ray tube 23 and interposed between the X-ray tube 23 and the X-ray detector 27. More specifically, the X-ray movable stop 25 is arranged in front of the X-ray radiation window of the X-ray tube 23. The X-ray movable stop 25 is also called an irradiation field limiter. The X-ray movable stop 25 narrows a maximum-aperture irradiation range (to be referred to as a maximum irradiation range hereinafter) to a predetermined irradiation range to prevent unwanted exposure of a portion except for an imaging portion intended by the operator to X-rays generated by the X-ray tube 23.

The X-ray movable stop 25 includes a plurality of first aperture blades movable in the first direction, and a plurality of second aperture blades movable in the second direction. Each of the first and second aperture blades is made of lead which cuts off X-rays generated by the X-ray tube 23. Note that the X-ray movable stop 25 may include a plurality of filters (added filters) inserted in the irradiation field of X-rays (to be referred to as an X-ray irradiation field hereinafter), in order to reduce the exposure dose to an object P and improve the image quality.

The X-ray detector 27 detects X-rays which have been generated by the X-ray tube 23 and passed through the object P. For example, the X-ray detector 27 is a flat panel detector (to be referred to as an FPD hereinafter). The FPD 27 includes a plurality of semiconductor detection elements. The semiconductor detection elements are classified into a direct conversion type and indirect conversion type. In direct conversion, incident X-rays are directly converted into an electrical signal. In indirect conversion, incident X-rays are converted into light by a phosphor and then the light is converted into an electrical signal.

Electrical signals generated in the plurality of semiconductor detection elements upon irradiation with X-rays are output to an analog to digital converter (to be referred to as an A/D converter hereinafter: not shown). The A/D converter converts an electrical signal into digital data. The A/D converter outputs digital data to a pre-processing unit (not shown). As the X-ray detector 27, an image intensifier or the like may be used.

The support mechanism 29 supports the X-ray tube 23, X-ray movable stop 25, and X-ray detector 27 to be movable. More specifically, the support mechanism 29 includes, for example, a C-arm and C-arm support portion (neither is shown). The C-arm mounts the X-ray tube 23 and X-ray movable stop 25, and the X-ray detector 27 to face each other. Instead of the C-arm, an Ω-arm is also usable. The C-arm support portion supports the C-arm to be slidable in a direction along the C shape. Also, the C-arm support portion supports the C-arm to be rotatable about the connecting portion between the C-arm and the C-arm support portion in a direction perpendicular to the direction along the C shape.

Note that the C-arm support portion can also support the C-arm to be able to translate in the first and second directions. The C-arm supports the X-ray tube 23, X-ray movable stop 25, and X-ray detector 27 to be able to change the distance (source image distance: to be referred to as an SID hereinafter) between the tube focus of the X-ray tube 23 and the X-ray detection surface of the X-ray detector 27. The X-ray diagnostic apparatus 5 including the C-arm support portion is used to, for example, image the circulatory system of the object P.

Note that the support mechanism 29 may support the X-ray tube 23, X-ray movable stop 25, and X-ray detector 27 to be movable along the x-, y-, and z-axes. At this time, the X-ray diagnostic apparatus 5 is used to, for example, image the digestive system and respiratory system of the object P. Note that the X-ray diagnostic apparatus 5 is not limited to the application purpose of diagnosis and may be an arbitrary X-ray diagnostic apparatus.

The support mechanism driving unit 31 drives the support mechanism 29 under the control of the control unit 43 (to be described later). More specifically, the support mechanism driving unit 31 supplies, to the C-arm support portion, a driving signal complying with a control signal from the control unit 43 to slide the C-arm in the direction along the C shape and rotate it in a direction (cranial direction (CRA) or caudal direction (CAU)) perpendicular to the direction along the C shape. In X-ray imaging, the object P set on the top 32 is interposed between the X-ray tube 23 and the X-ray detector 27.

The pre-processing unit (not shown) executes pre-processing for digital data output from the X-ray detector 27. The pre-processing includes correction of sensitivity non-uniformity between channels in the X-ray detector 27, and correction of extreme signal drop or data omission caused by an X-ray strong absorber such as a metal. The pre-processed digital data is output to the image generation unit 33 (to be described below).

The image generation unit 33 generates an X-ray image based on the digital data pre-processed after X-ray imaging. The image generation unit 33 outputs the generated X-ray image to the storage unit 12, display unit 14, and blood flow information generation unit 15 (to be described later).

The I/F 11 is an interface regarding a network, an external storage device (not shown), another medical image diagnostic apparatus, a medical image processing apparatus 10, and the like. Data such as an X-ray image obtained by the X-ray diagnostic apparatus 5, an analysis result, and the like can be transferred to another apparatus via the I/F 11 and a network.

The storage unit 12 stores various data groups such as various X-ray images generated by the image generation unit 33, the control program of the X-ray diagnostic apparatus 5, a diagnostic protocol, an operator instruction sent from the operation unit 13 (to be described later), imaging conditions, and fluoroscopic conditions. For example, the storage unit 12 stores data of a plurality of X-ray images (to be referred to as data of a series of images hereinafter) which are obtained by temporally successively imaging an organ of the object P and correspond to the respective X-ray imaging operations. Data of the series of images are data of a plurality of images collected during a period till the completion of outflow of a contrast medium from the object P after the start of inflow of the contrast medium into the object P. The organ is, e.g., the heart. Note that the organ is not limited to the heart and may be another organ such as the liver or brain. For descriptive convenience, assume that the organ is the heart. Data of a series of images are images regarding the imaging of an object to which a tracer (for example, contrast medium) is given for, e.g., coronary angiography.

The storage unit 12 stores the position of a region of interest set on an X-ray image, a region (to be referred to as the first region hereinafter) dominated by a downstream blood vessel (to be referred to as a stenosed blood vessel hereinafter) from a stenosed portion, a region (to be referred to as the second region hereinafter) dominated by a blood vessel (to be referred to as an unstenosed blood vessel hereinafter) having an unstenosed portion, an SID, and the like. The first and second regions are different regions. The first and second regions to be stored are input from the operation unit 13 (to be described later). Note that the storage unit 12 may store a program (blood flow inhibition index generation program) regarding a blood flow inhibition index generation function (to be described later).

The storage unit 12 stores the extractions of blood flow volumes respectively extracted from capillary blood vessels of the artery to the first and second regions. These extractions are equivalent to predetermined correction coefficients for correcting a blood flow inhibition index (to be described later). More specifically, the storage unit 12 stores, as the predetermined correction coefficient, an extraction $E_{stenosed}$ (to be referred to as the first correction coefficient hereinafter) of a blood flow volume extracted from capillary blood vessels at the downstream portion of a stenosed blood vessel to the first region. Also, the storage unit 12 stores, as the predetermined correction coefficient, an extraction $E_{remote}$ (to be referred to as the second correction coefficient hereinafter) of a blood flow volume extracted from capillary blood vessels at the downstream portion of an unstenosed blood vessel to the second region. The storage unit 12 stores the predetermined correction coefficients as a correspondence table (lookup table) for each organ and each of the set first and second regions.

Note that the storage unit 12 may store a predetermined fixed value used in the blood flow information generation unit 15 when generating blood flow information in each of the first and second regions. The predetermined fixed value is, e.g., a permeability surface area product (to be referred to as PS hereinafter).

The display unit 14 displays an X-ray image generated by the image generation unit 33. The display unit 14 displays an input screen for inputting imaging conditions in X-ray imaging and the first and second regions. Together with an X-ray image and the first and second regions, the display unit 14 displays a blood flow inhibition index generated by the blood flow inhibition index generation unit 16 (to be described later).

The operation unit 13 is used to input a region of interest, SID, imaging conditions in X-ray imaging, the first and second regions, activation of the blood flow inhibition index generation program, and the like. More specifically, the operation unit 13 inputs various instructions, commands, information, selections, and settings from the operator to the X-ray diagnostic apparatus 5. Although not shown, the operation unit 13 includes a track ball for performing, e.g., setting of a region of interest and the first and second regions, a switch button which triggers the start of X-ray imaging, a mouse, and a keyboard. The operation unit 13 detects the coordinate point of a cursor displayed on the display screen, and outputs the detected coordinate point to the control unit 43 (to be described later). Note that the operation unit 13 may be a touch panel arranged to cover the display screen. In this case, the operation unit 13 detects a touched and indicated coordinate point based on a coordinate reading principle such as an electromagnetic induction method, electromagnetic distortion method, or pressure sensitive method, and outputs the detected coordinate point to the control unit 43.

The operation unit 13 outputs, to the blood flow information generation unit 15 (to be described later), the positions (coordinate points in an orthogonal coordinate system) of the first and second regions input on an X-ray image. Note that the operation unit 13 may be used to input an instruction (index calculation instruction) for calculating a blood flow inhibition index.

The control unit 43 includes a CPU (Central Processing Unit) and memory (neither is shown). The control unit 43 controls the respective units in the X-ray diagnostic apparatus 5 in accordance with an operator instruction, imaging conditions, and the like sent from the operation unit 13 in order to execute X-ray imaging. In response to input of the first and second regions and input of an index calculation instruction, the control unit 43 controls the blood flow information generation unit 15 and blood flow inhibition index generation unit 16.

The blood flow information generation unit (tissue blood flow calculation unit) 15 generates the first blood flow information of the first region and the second blood flow information of the second region based on data of a series of images stored in the storage unit 12. The first blood flow information is, e.g., a myocardial blood flow (to be referred to as a first value $MBF_{stenosed}$ hereinafter) corresponding to the first region. The second blood flow information is, e.g., a myocardial blood flow (to be referred to as a second value $MBF_{remote}$ hereinafter) corresponding to the second region.

More specifically, the blood flow information generation unit 15 generates a local blood flow volume (to be referred to as a first local blood flow volume $K_{1stenosed}$ hereinafter) entering the first region from a stenosed blood vessel, based on a temporal change of the density of a pixel value caused by the contrast medium in the first region in data of a series of images. In addition, the blood flow information generation unit 15 generates a local blood flow volume (to be referred to as a second local blood flow volume $K_{1remote}$ hereinafter) entering the second region from an unstenosed blood vessel, based on a temporal change of the density of a pixel value caused by the contrast medium in the second region. More specifically, the blood flow information generation unit 15 subtracts, from a series of images, a so-called mask image in which the contrast medium does not flow. A series of difference images represent a stain distribution (contrast medium distribution) by the contrast medium. Pixel values in the series of difference images indicate contrast medium concentrations. The first local blood flow volume $K_{1stenosed}$ is equivalent to the transfer constant of the contrast medium from the stenosed blood vessel to the first region. The second local blood flow volume $K_{1remote}$ is equivalent to the transfer constant of the contrast medium from the unstenosed blood vessel to the second region.

More specifically, the blood flow information generation unit 15 sets a plurality of local partial regions in a lattice in the first and second regions in each of the series of difference images. Based on the series of difference images, the blood flow information generation unit 15 generates a time-to-density curve for the respective local partial regions. The blood flow information generation unit 15 generates the first local blood flow volume $K_{1stenosed}$ and second local blood flow volume $K_{1remote}$ based on a model analysis-based theory and the time-to-density curve.

The blood flow information generation unit 15 calculates the first value $MBF_{stenosed}$ by correcting the first local blood flow volume $K_{1stenosed}$ by a first correction coefficient $E_{stenosed}$. More specifically, the blood flow information generation unit 15 generates the first value $MBF_{stenosed}$ by dividing the first local blood flow volume $K_{1stenosed}$ by the first correction coefficient $E_{stenosed}$. The blood flow information generation unit 15 calculates the second value $MBF_{remote}$ by correcting the second local blood flow volume $K_{1remote}$ by a second correction coefficient $E_{remote}$. More specifically, the blood flow information generation unit 15 generates the second value $MBF_{remote}$ by dividing the second local blood flow volume $K_{1remote}$ by the second correction coefficient $E_{remote}$. The blood flow information generation unit 15 outputs, to the blood flow inhibition index generation unit (to be described later), the first value $MBF_{stenosed}$ corresponding to the generated first blood flow information and the second value $MBF_{remote}$ corresponding to the second blood flow information.

Note that the blood flow information generation unit 15 may calculate the first value $MBF_{stenosed}$ based on the fixed value PS and the first local blood flow volume $K_{1stenosed}$. Also, the blood flow information generation unit 15 may calculate the second value $MBF_{remote}$ based on the fixed value PS and the second local blood flow volume $K_{1remote}$.

Based on the first blood flow information and second blood flow information, the blood flow inhibition index generation unit 16 generates a blood flow inhibition index representing the degree of inhibition of a blood flow in a blood vessel regarding the first or second region. For example, based on the first blood flow information and second blood flow information, the blood flow inhibition index generation unit 16 generates a blood flow inhibition index regarding a stenosed blood vessel. Specifically, the blood flow inhibition index generation unit 16 generates, as the blood flow inhibition index, the ratio of the first value $MBF_{stenosed}$ and second value $MBF_{remote}$. More specifically, the blood flow inhibition index generation unit 16 generates a blood flow inhibition index in the first region by dividing the first value $MBF_{stenosed}$ by the second value $MBF_{remote}$. The blood flow inhibition index is an index equivalent to, e.g., a fractional flow reserve (to be referred to as FFR hereinafter).

FFR is a value obtained by normalizing, that is, dividing the blood flow volume of a stenosed blood vessel (to be referred to as a stenosed blood vessel blood flow volume $Q_{stenosed}$ hereinafter) by the blood flow volume ($Q_{normal}$) of a blood vessel assumed not to be stenosed. FFR is defined by:

$$FFR \equiv Q_{stenosed}/Q_{normal} \quad (1)$$

The pressure in a blood vessel is correlated with the blood flow volume. The blood flow volume of a blood vessel is equivalent in principle to the volume of a blood flowing through a tissue S (for example, part of the myocardium: to be simply referred to as a "myocardial portion" hereinafter) under the domination of this blood vessel. Letting MBF be the local blood flow volume, equation (1) can be rewritten into:

$$FFR \equiv Q_{stenosed}/Q_{normal} = \Sigma MBF_{stenosed}/\Sigma MBF_{normal} \quad (2)$$

where $MBF_{stenosed}$ is the local blood flow volume of the myocardial portion suspected of ischemia under the domination of the stenosed blood vessel, and $\Sigma MBF_{stenosed}$ is the blood flow volume of the entire myocardial portion under the domination of the stenosed blood vessel. That is, the summation sign $\Sigma$ of $\Sigma MBF_{stenosed}$ indicates the summation of $MBF_{stenosed}$ for the entire myocardial portion under the domination of the stenosed blood vessel. Similarly, $MBF_{normal}$ is the normal local blood flow volume of the same myocardial portion when there is no stenosis, and $\Sigma MBF_{normal}$ is the entire normal blood flow volume of the normal myocardial portion. The summation sign $\Sigma$ of $\Sigma MBF_{normal}$ indicates the summation of $MBF_{normal}$ for the entire same myocardial portion when there is no stenosis.

When S represents the volume of the myocardial portion, and $MBF_{stenosed}$ and $MBF_{normal}$ are replaced with the average values of local blood flow volumes in the respective regions for convenience, equation (2) can be rewritten into:

$$FFR \equiv Q_{stenosed}/Q_{normal} = \Sigma MBF_{stenosed}/\Sigma MBF_{normal} = \quad (3)$$
$$(S \cdot MBF_{stenosed})/(S \cdot MBF_{normal}) = MBF_{stenosed}/MBF_{normal}$$

Here, when the average blood flow volume $MBF_{normal}$ of the myocardium on the assumption that there is no stenosis is considered to be equal to the average blood flow volume $MBF_{remote}$ of a blood vessel dominated by an actually unstenosed blood vessel and is replaced by it, equation (3) can be rewritten into:

$$FFR \equiv Q_{stenosed}/Q_{normal} = \Sigma MBF_{stenosed}/\Sigma MBF_{normal} =$$
$$(S \cdot MBF_{stenosed})/(S \cdot MBF_{normal}) = MBF_{stenosed}/MBF_{normal}$$
$$FFR' = MBF_{stenosed}/MBF_{remote}$$

By this replacement, FFR is replaced with an index FFR' equivalent to FFR. The index FFR' equivalent to FFR corresponds to a blood flow inhibition index.

Let $K_1$ be the local blood flow volume calculated from image information, $K_{1stenosed}$ be the average value of the local blood flow volume of a stenosis-dominated region calculated from image information, and $K_{1remote}$ be the average value of a local blood flow volume calculated from image information in regard to a region dominated by an unstenosed blood vessel different from the stenosed blood vessel. Then, equation (3) can be rewritten into:

$$FFR \equiv Q_{stenosed}/Q_{normal} = \Sigma MBF_{stenosed}/\Sigma MBF_{normal} = \quad (4)$$
$$(S \cdot MBF_{stenosed})/(S \cdot MBF_{normal}) = MBF_{stenosed}/MBF_{normal}$$
$$FFR' = MBF_{stenosed}/MBF_{remote}$$
$$= (K_{1stenosed}/E_{stenosed})/(K_{1remote}/E_{remote})$$

where $E_{stenosed}$ and $E_{remote}$ are correction coefficients. For example, values of 0.5 and 0.6 are selected as $E_{stenosed}$ and $E_{remote}$.

At this time, the correction coefficient E may be calculated from a relation: $E=(1-\exp(-PS/MBF))$ using MBF and PS. It is therefore possible to calculate MBF from only $K_1$ using the following equations (5) and (6), and calculate FFR' according to equation (3):

$$MBF_{stenosed}=K_{1stenosed}/(1-\exp(-PS/MBF_{stenosed})) \quad (5)$$

$$MBF_{remote}=K_{1remote}/(1-\exp(-PS/MBF_{remote})) \quad (6)$$

The blood flow inhibition index generation unit 16 outputs the generated blood flow inhibition index FFR' to the display unit 14.

(Blood Flow Inhibition Index Generation Function)

The blood flow inhibition index generation function is a function of generating the first blood flow information and second blood flow information based on data of a series of images, and generating a blood flow inhibition index in the first or second region based on the generated first blood flow information and second blood flow information. Processing regarding the blood flow inhibition index generation function (to be referred to as blood flow inhibition index generation processing hereinafter) will be explained below.

Figure 8:
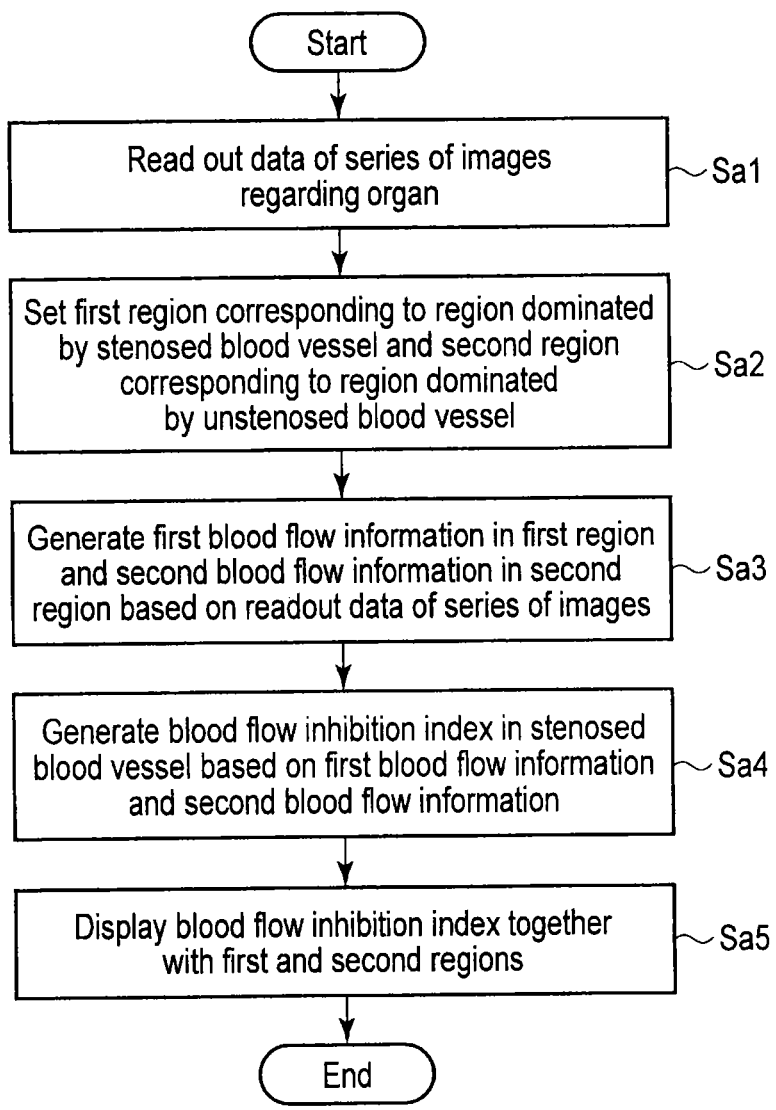
FIG. 8 is a flowchart showing the procedures of a blood flow inhibition index generation function in the X-ray diagnostic apparatus according to the medical image diagnostic apparatus of the embodiment.

FIG. 8 is a flowchart showing an example of the procedures of blood flow inhibition index generation processing.

Data of a series of images regarding an organ of an object are read out from the storage unit 12 (step Sa1). The first region corresponding to a region dominated by a stenosed blood vessel and the second region corresponding to a region dominated by an unstenosed blood vessel are set in accordance with an operator instruction via the operation unit 13 (step Sa2). Based on the readout data of the series of images, the first blood flow information in the first region and the second blood flow information in the second region are generated (step Sa3). Based on the first blood flow information and second blood flow information, blood flow inhibition indices in the stenosed blood vessel are generated (step Sa4). For both the first and second regions, the blood flow inhibition indices are displayed (step Sa5).

(Modification)

A difference from the first embodiment is that pieces of blood flow information corresponding to respective pixels in regions different from the first and second regions are generated. Based on the pieces of blood flow information corresponding to the respective pixels, blood flow inhibition indices corresponding to the respective pixels are generated. The blood flow inhibition indices are displayed in hues corresponding to the values of the blood flow inhibition indices for the respective pixels.

Based on data of a series of images, the blood flow information generation unit 15 generates pieces of blood flow information corresponding to respective pixels in regions different from the first and second regions. The blood flow information generation unit 15 outputs, to the blood flow inhibition index generation unit 16, the pieces of blood flow information corresponding to the respective pixels.

Based on the pieces of blood flow information corresponding to the respective pixels, the blood flow inhibition index generation unit 16 generates blood flow inhibition indices corresponding to the respective pixels. More specifically, the blood flow inhibition index generation unit 16 calculates the blood flow inhibition indices by using, for example, the second value as the denominator of the blood flow inhibition index FFR' and the pieces of blood flow information of the respective pixels as the numerator. In other words, the blood flow inhibition index generation unit 16 generates the blood flow inhibition indices of the respective pixels by using, as a reference, a value equivalent to the blood flow volume of a blood vessel in the second region. The blood flow inhibition index generation unit 16 outputs, to the display unit 14, the plurality of blood flow inhibition indices corresponding to the respective pixels.

The storage unit 12 stores a plurality of hues corresponding to the values of the blood flow inhibition indices.

Figure 9:
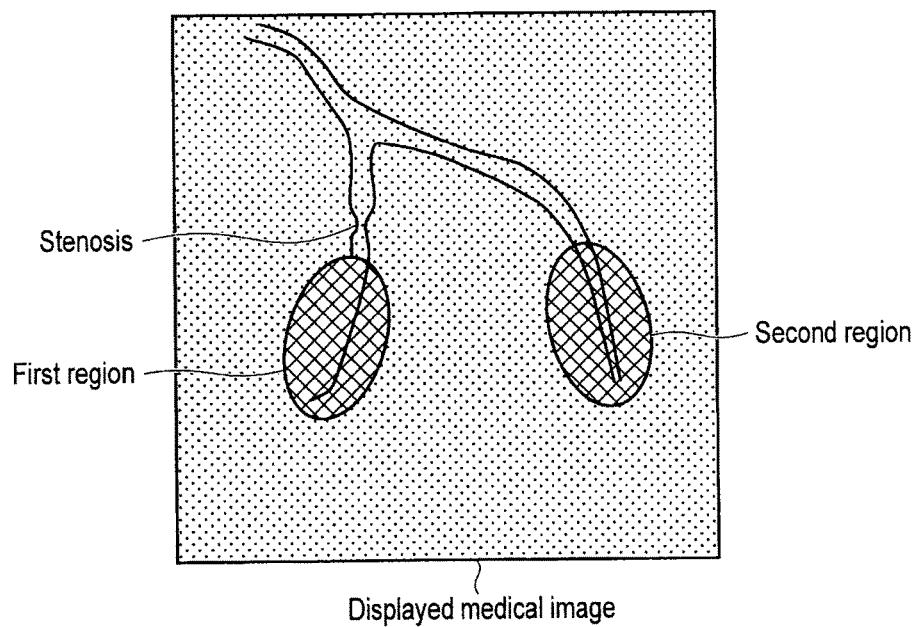
FIG. 9 is a view showing a display example in which blood flow inhibition indices are displayed in respective pixels according to a modification of the embodiment.

The display unit 14 displays the plurality of blood flow inhibition indices corresponding to the respective pixels, in a plurality of hues corresponding to the values of the blood flow inhibition indices for the respective pixels. Note that the display unit 14 may display the plurality of blood flow inhibition indices in hues corresponding to the blood flow inhibition indices together with at least either the first or second region, as shown in FIG. 9. At this time, the display unit 14 displays a scalar field having the blood flow inhibition indices as scalars. Note that the blood flow inhibition index may be displayed by gray scale gradation. The graph display of the blood flow inhibition indices (FFR' values) is merely an example, and the embodiment is not limited to the above-mentioned example. For example, in the embodiment, FFR' values (blood flow inhibition indices) may be displayed in a predetermined chart form.

The above-described arrangement can yield the following effects.

Figure 2:
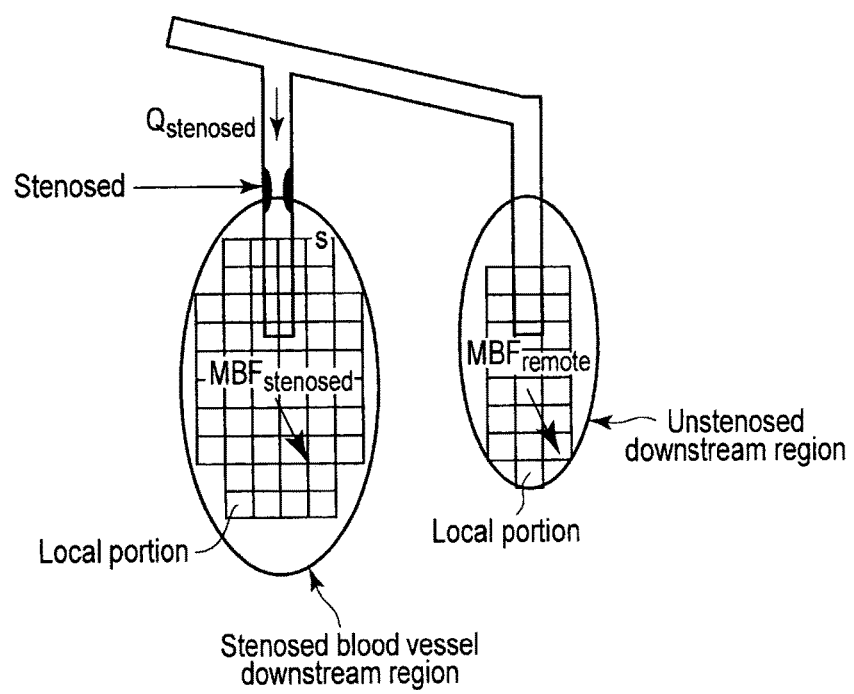
FIG. 2 is a supplementary explanatory view of a principle of obtaining an index equivalent to FFR from image data according to the embodiment.

In the X-ray diagnostic apparatus 5 according to the embodiment, as shown in FIG. 2, the blood flow volume of a blood vessel is alternatively obtained from a tissue blood flow volume. The normal local blood flow volume $MBF_{normal}$ of the same myocardial portion when there is no stenosis is substituted by the local blood flow volume $K_{1remote}$ calculated from image information regarding a region dominated by an unstenosed blood vessel different from the stenosed blood vessel in the image. That is, a local blood flow volume used as the denominator is obtained not from a normal value as in equation (3), but actually from data of a series of images, and is further obtained from a region dominated by an unstenosed blood vessel different from the stenosed blood vessel. This can suppress image-specific reliability degradation factors in regard to the generation of the blood flow inhibition index FFR', and can improve the reliability.

According to the modification of the embodiment, blood flow inhibition indices corresponding to respective pixels can be generated based on pieces of blood flow information corresponding to the respective pixels. The blood flow inhibition indices can be displayed in hues corresponding to the values of the blood flow inhibition indices for the respective pixels. The blood flow inhibition indices can therefore be displayed in the entire image, increasing the diagnostic efficiency for the object P.

Hence, the X-ray diagnostic apparatus 5 according to the embodiment can obtain an index (blood flow inhibition index) equivalent to FFR from image data without inserting a wire.

(Second Embodiment)

The second embodiment is different from the first embodiment in that the medical image diagnostic apparatus is an X-ray computed tomography (to be referred to as a CT hereinafter) apparatus (to be also referred to as an X-ray CT apparatus hereinafter). Note that there are various types of X-ray computed tomography apparatuses such as Rotate/Rotate-Type in which an X-ray tube and X-ray detector integrally rotate around an object, and Stationary/Rotate-Type in which many X-ray detection elements arrayed in a ring shape are fixed and only an X-ray tube rotates around an object. Any type of X-ray computed tomography apparatus is applicable to the embodiment.

Reconstruction of an image requires projection data for 360° corresponding to one round around an object. Even the half-scan method requires projection data for 180°+fan angle. Either reconstruction method is applicable to the embodiment. As for a mechanism of changing incident X-rays into charges, indirect conversion and direct conversion are mainstream. In indirect conversion, X-rays are converted into light by a phosphor such as a scintillator, and the light is further converted into charges by a photoelectric converter such as a photodiode. Direct conversion exploits generation of electron-hole pairs in a semiconductor such as selenium by X-rays, and movement of them to an electrode, i.e., photoconductive phenomenon. As an X-ray detection element, either of these methods can be used.

Recently, so-called multi-tube X-ray computed tomography apparatuses in which a plurality of pairs each of an X-ray tube and X-ray detector are mounted on a rotating frame are being commercialized, and their peripheral techniques are being developed. In the embodiment, both of a conventional single-tube X-ray computed tomography apparatus and multi-tube X-ray computed tomography apparatus are applicable. In the multi-tube type, a plurality of tube voltages to be applied to respective tubes are different (multi-tube method). Here, the single-tube type will be explained.

The X-ray detection element may be a two-layered detection element having a front detection portion which detects low-energy X-rays, and a rear detection portion which is arranged on the rear surface of the front detector and detects high-energy X-rays. For descriptive convenience, assume that the X-ray detector is a single-layered X-ray detection element.

FIG. 10 is a view showing an example of the arrangement of an X-ray computed tomography apparatus 4 according to a medical image diagnostic apparatus of the embodiment. The X-ray computed tomography apparatus 4 includes a gantry unit 100, pre-processing unit 200, reconstruction unit 500, interface (I/F) unit 11, storage unit 12, display unit 14, operation unit 13, control unit 900, blood flow information generation unit 15, and blood flow inhibition index generation unit 16. The I/F 11 connects the X-ray computed tomography apparatus 4 to an electronic communication line (to be referred to as a network hereinafter). A radiation section information management system, a hospital information system, another medical image diagnostic apparatus, a medical image processing apparatus 10, and the like (none are shown) are connected to the network.

The gantry unit 100 houses a rotation support mechanism (not shown). The rotation support mechanism includes a rotating frame 101, a frame support mechanism which supports the rotating frame 101 to be freely rotatable about the rotation axis Z, and a rotation driving unit (motor) 103 which drives the rotating frame 101 to rotate.

The rotating frame 101 mounts an X-ray generation unit 105 which generates X-rays under the control of the control unit 900 (to be described later), a two-dimensional array or multi-array X-ray detection unit (to be referred to as an area detector hereinafter) 115, a data acquisition system (to be referred to as a DAS hereinafter) 121, a non-contact data transmission unit 123, a cooling device and gantry control device (neither is shown), and the like.

The rotation driving unit 103 rotates the rotating frame 101 at a predetermined rotational speed in accordance with a driving signal from the control unit 900 (to be described later).

The X-ray generation unit 105 includes a high-voltage generator 107 and X-ray tube 109. Under the control of the control unit 900 (to be described later), the high-voltage generator 107 generates a tube voltage to be applied to the X-ray tube 109 and a tube current to be supplied to the X-ray tube 109, by using power supplied via a slip ring 111. Note that the high-voltage generator 107 may be arranged outside the gantry unit 100. At this time, the high-voltage generator 107 applies a tube voltage to the X-ray tube 109 via the slip ring 111 and supplies a tube current to the X-ray tube 109.

Upon application of the tube voltage and supply of the tube current from the high-voltage generator 107, the X-ray tube 109 radiates X-rays from the X-ray focus. A collimator (not shown) is arranged in an X-ray radiation window in the front surface of the X-ray tube 109. The collimator includes a plurality of collimator plates. The plurality of collimator plates shape X-rays radiated from the X-ray focus in the X-ray tube 109 into, e.g., a cone beam form (pyramidal form). More specifically, the control unit 900 (to be described later) drives the plurality of collimator plates to obtain a cone angle for obtaining projection data of actual measurement of a preset slice thickness. Further, at least two collimator plates (to be referred to as a cone angle collimator hereinafter) out of the plurality of collimator plates are independently driven for an opening width regarding the cone angle under the control of the control unit 900.

The X-ray radiation range is indicated by a dotted line 113 in FIG. 10. The X-axis is a straight line which is perpendicular to the rotation axis Z and is upward in the vertical direction. The Y-axis is a straight line perpendicular to the X-axis and rotation axis Z.

The area detector 115 detects X-rays having passed through an object. The area detector 115 is attached to the rotating frame 101 at a position and angle at which the area detector 115 faces the X-ray tube 109 via the rotation axis Z. The area detector 115 includes a plurality of X-ray detection elements. The following description assumes that a single X-ray detection element forms a single channel. A plurality of channels are perpendicular to the rotation axis Z and uses the focus of radiated X-rays as the center. The channels are two-dimensionally arrayed in two directions, i.e., a slice direction and the direction of an arc (channel direction) whose radius is the distance from this center to the center of the light-receiving unit of an X-ray detection element for one channel. The two-dimensional array is constructed by arranging, in the slice direction, a plurality of arrays each of a plurality of channels arrayed one-dimensionally in the channel direction.

The area detector 115 having this two-dimensional X-ray detection element array may be constructed by arranging, in the slice direction, a plurality of arrays each of a plurality of above-described modules arrayed one-dimensionally in an almost arc direction. Alternatively, the area detector 115 may be constructed by a plurality of modules each obtained by arraying a plurality of X-ray detection elements in one line. At this time, the respective modules are arrayed one-dimensionally in an almost arc direction along the channel direction. The number of X-ray detection elements arrayed in the slice direction will be called the number of columns.

At the time of scanning for X-ray imaging or X-ray computed tomography of an object, the object is set on a top 32 and inserted into a cylindrical imaging region 117 between the X-ray tube 109 and the area detector 115. The data acquisition system (to be referred to as a DAS hereinafter) 121 is connected to the output side of the area detector 115. In CT scanning, the object is set on the top 32 and moved into the imaging region 117.

In the DAS 121, an I-V converter which converts the current signal of each channel of the area detector 115 into a voltage, an integrator which integrates the voltage signal cyclically in synchronism with the X-ray exposure cycle, an amplifier which amplifies an output signal from the integrator, and an analog to digital converter which converts an output signal from the amplifier into a digital signal are attached for each channel. The DAS 121 changes the integration interval in the integrator in accordance with scanning under the control of the control unit 900 (to be described later). Data (pure raw data) output from the DAS 121 is transmitted to the pre-processing unit 200 (to be described later) via the non-contact data transmission unit 123 using magnetic transmission/reception or light transmission/reception.

The pre-processing unit 200 generates projection data based on the pure raw data output from the DAS 121. More specifically, the pre-processing unit 200 performs pre-processing for the pure raw data. The pre-processing includes, e.g., processing of correcting sensitivity nonuniformity between channels, and processing of correcting extreme signal intensity drop or signal omission caused by an X-ray strong absorber, mainly by a metal portion. Data (raw data or projection data: to be referred to as projection data here) immediately before reconstruction processing that is output from the pre-processing unit 200 is stored, in association with a view angle obtained upon data acquisition, in the storage unit 12 including a magnetic disk, magneto-optical disk, or semiconductor memory.

For descriptive convenience, a set of projection data in a plurality of channels that have been acquired and interpolated almost simultaneously by one shot, have the same view angle, and are defined by the cone angle will be called a projection data set. The view angle is an angle representing each position on a circular orbit on which the X-ray tube 109 rotates about the rotation axis Z, in the range of 360° using, as 0°, the top of the circular orbit in the upward direction perpendicular to the rotation axis Z. Note that projection data for each channel of the projection data set is identified by the view angle, cone angle, and channel number.

The reconstruction unit 500 has a function of reconstructing an almost columnar three-dimensional image (volume data) regarding a reconstruction region by a feldkamp method or cone beam reconstruction method based on a projection data set for which the view angle falls within the range of 360° or 180°+fan angle. The reconstruction unit 500 has a function of reconstructing a two-dimensional image (tomographic image) by, e.g., a fan beam reconstruction method (also called a fan beam convolution back projection method) or a filtered back projection method. The feldkamp method is a reconstruction method used when projection rays cross each other with respect to the reconstruction plane, similar to cone beams. The feldkamp method is an approximate image reconstruction method in which rays are regarded as fan projection beams in convolution on the premise that the cone angle is small, and back projection is processed along rays in scanning. The cone beam reconstruction method is a reconstruction method of correcting projection data in accordance with the angle of a ray with respect to the reconstruction plane as a method capable of suppressing a cone angle error compared to the feldkamp method.

Based on volume data, the reconstruction unit 500 reconstructs a medical image to be displayed on the display unit 14. The medical image is generated by various image processes such as volume rendering, surface rendering, and planar reconstruction.

The storage unit 12 stores a medical image (to be referred to as a reconstructed image hereinafter) reconstructed by the reconstruction unit 500, a plurality of projection data sets, and the like. Also, the storage unit 12 stores volume data (to be referred to as perfusion volume data hereinafter) representing perfusion regarding an organ of an object. For descriptive convenience, assume that the organ is the heart. Note that the organ is not limited to the heart, and may be another organ such as the liver or brain. The perfusion volume data is volume data representing, e.g., the mean-transit-time (MTT) for which a contrast medium passes through each voxel in volume data.

The storage unit 12 stores information such as an operator instruction input from the operation unit 13 (to be described later), image processing conditions, and imaging conditions. The storage unit 12 stores a control program for controlling the gantry unit 100, a bed, and the like for X-ray computed tomography or CT perfusion imaging.

Further, the storage unit 12 stores the position of a region of interest set on a medical image regarding displayed volume data or perfusion volume data, a region (first region) dominated by a stenosed blood vessel, a region (second region) dominated by an unstenosed blood vessel, and the like. The first and second regions are different regions. The first and second regions to be stored are input from the operation unit 13 (to be described later). Note that the storage unit 12 may store a program (blood flow inhibition index generation program) regarding a blood flow inhibition index generation function (to be described later).

The storage unit 12 stores predetermined correction coefficients ($E_{stenosed}$: first correction coefficient, and $E_{remote}$: second correction coefficient) for correcting a blood flow inhibition index. The storage unit 12 stores the predetermined correction coefficients as a correspondence table (lookup table) for each organ and each of the set first and second regions. Note that the storage unit 12 may store a predetermined fixed value (PS).

The display unit 14 displays a medical image generated by the reconstruction unit 500. The display unit 14 displays an input screen for inputting imaging conditions for X-ray computed tomography or CT perfusion imaging, and the first and second regions. Together with a medical image and the first and second regions, the display unit 14 displays a blood flow inhibition index generated by the blood flow inhibition index generation unit 16.

The operation unit 13 is used to input a region of interest, imaging conditions for X-ray computed tomography or CT perfusion imaging, the first and second regions, activation of the blood flow inhibition index generation program, and the like. More specifically, the operation unit 13 inputs various instructions, commands, information, selections, and settings from the operator to the X-ray computed tomography apparatus 4. The various input instructions, commands, information, selections, and settings are output to the control unit 900 (to be described later) and the like. Although not shown, the operation unit 13 includes a track ball for performing, e.g., setting of a region of interest and the first and second regions, a switch button which triggers the start of X-ray imaging, a mouse, and a keyboard. The operation unit 13 detects the coordinate point of a cursor displayed on the display screen, and outputs the detected coordinate point to the control unit 900 (to be described later). Note that the operation unit 13 may be a touch panel arranged to cover the display screen. In this case, the operation unit 13 detects a touched and indicated coordinate point based on a coordinate reading principle such as an electromagnetic induction method, electromagnetic distortion method, or pressure sensitive method, and outputs the detected coordinate point to the control unit 900.

The operation unit 13 outputs, to the blood flow information generation unit 15 (to be described later), the positions (coordinate points in an orthogonal coordinate system) of the first and second regions input on an X-ray image. Note that the operation unit 13 may be used to input an instruction (index calculation instruction) for calculating a blood flow inhibition index.

The display unit 14 displays, e.g., a medical image reconstructed by the reconstruction unit 500, and an input screen for inputting scan conditions set for X-ray computed tomography, reconstruction conditions regarding reconstruction processing, and the like. Together with the first and second regions, the display unit 14 displays a blood flow inhibition index on the medical image.

The bed (not shown) includes the top 32, a support frame (not shown) which supports the top 32 to be movable in the Z direction, and a driving unit (not shown) which drives the top 32 and bed. The driving unit moves the bed up and down in accordance with an input based on an operator instruction. The driving unit moves the top 32 in the Z direction in accordance with an imaging plan input from the operation unit 13.

The control unit 900 functions as the core of the X-ray computed tomography apparatus 4. The control unit 900 includes a CPU (Central Processing Unit) and memory (neither is shown). The control unit 900 controls the high-voltage generator 107, gantry unit 100, and the like for X-ray computed tomography of an object based on inspection schedule data and a control program stored in a memory (not shown). More specifically, the control unit 900 temporarily stores, in the memory (not shown), an operator instruction sent from the operation unit 13 and the like. Based on the information temporarily stored in the memory, the control unit 900 controls the high-voltage generator 107, gantry unit 100, and the like. The control unit 900 reads out, from the storage unit 12, a control program for executing, e.g., generation and display of a predetermined image, expands it in the memory of the control unit 900, and executes calculations regarding various processes, processing, and the like. In response to input of the first and second regions and input of an index calculation instruction, the control unit 900 controls the blood flow information generation unit 15 and blood flow inhibition index generation unit 16.

The blood flow information generation unit (tissue blood flow calculation unit) 15 generates the first blood flow information of the first region and the second blood flow information of the second region based on volume data (perfusion volume data) stored in the storage unit 12. For example, based on perfusion volume data, the blood flow information generation unit 15 generates temporal changes of the densities of pixel values in the first and second regions caused by a contrast medium. The temporal changes of the densities of pixel values are the mean-transit-times (MTTs) for which the contrast medium passes through the first and second regions. The blood flow information generation unit 15 generates a first local blood flow volume $K_{1stenosed}$ based on, e.g., MTT in the first region. In addition, the blood flow information generation unit 15 generates a second local blood flow volume $K_{1remote}$ based on, e.g., MTT in the second region.

The blood flow information generation unit 15 calculates a first value $MBF_{stenosed}$ corresponding to the first blood flow information by correcting the first local blood flow volume $K_{1stenosed}$ by a first correction coefficient $E_{stenosed}$. More specifically, the blood flow information generation unit 15 generates the first value $MBF_{stenosed}$ by dividing the first local blood flow volume $K_{1stenosed}$ by the first correction coefficient $E_{stenosed}$. The blood flow information generation unit 15 calculates the second value $MBF_{remote}$ corresponding to the second blood flow information by correcting the second local blood flow volume $K_{1remote}$ by a second correction coefficient $E_{remote}$. More specifically, the blood flow information generation unit 15 generates the second value $MBF_{remote}$ by dividing the second local blood flow volume $K_{1remote}$ by the second correction coefficient $E_{remote}$. The blood flow information generation unit 15 outputs, to the blood flow inhibition index generation unit 16, the first value $MBF_{stenosed}$ corresponding to the generated first blood flow information and the second value $MBF_{remote}$ corresponding to the second blood flow information.

Note that the blood flow information generation unit 15 may calculate the first value $MBF_{stenosed}$ based on the fixed value PS and the first local blood flow volume $K_{1stenosed}$. Also, the blood flow information generation unit 15 may calculate the second value $MBF_{remote}$ based on the fixed value PS and the second local blood flow volume $K_{1remote}$.

Based on the first blood flow information and second blood flow information, the blood flow inhibition index generation unit 16 generates a blood flow inhibition index representing the degree of inhibition of a blood flow in a blood vessel regarding the first or second region. For example, based on the first blood flow information and second blood flow information, the blood flow inhibition index generation unit 16 generates a blood flow inhibition index regarding a stenosed blood vessel. Specifically, the blood flow inhibition index generation unit 16 generates, as the blood flow inhibition index, the ratio of the first value $MBF_{stenosed}$ and second value $MBF_{remote}$. More specifically, the blood flow inhibition index generation unit 16 generates a blood flow inhibition index in the first region by dividing the first value $MBF_{stenosed}$ by the second value $MBF_{remote}$. The blood flow inhibition index is an index equivalent to, e.g., a fractional flow reserve (FFR). The relationship between the fractional flow reserve and the blood flow inhibition index is the same as that in the first embodiment, and a description thereof will not be repeated.

(Blood Flow Inhibition Index Generation Function)

The blood flow inhibition index generation function is a function of generating the first blood flow information and second blood flow information based on perfusion volume data, and generating a blood flow inhibition index in the first or second region based on the generated first blood flow information and second blood flow information. Processing regarding the blood flow inhibition index generation function (to be referred to as blood flow inhibition index generation processing hereinafter) will be explained below.

Figure 11:
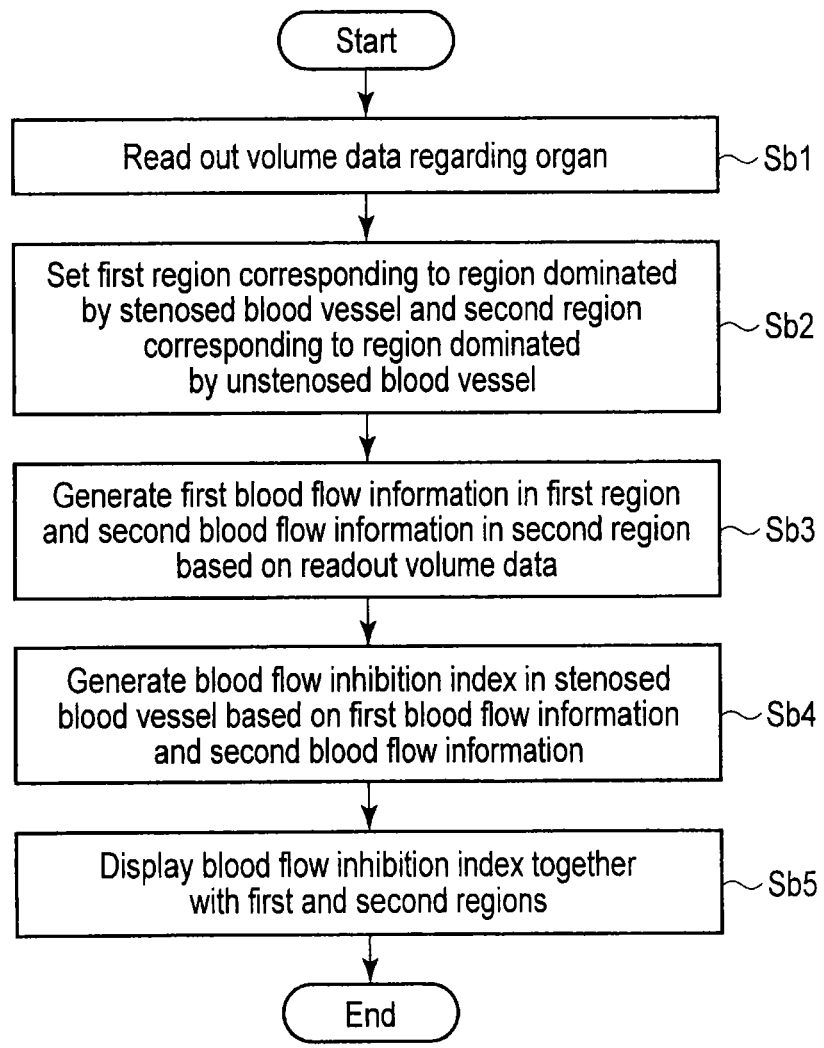
FIG. 11 is a flowchart showing the procedures of the blood flow inhibition index generation function in the X-ray computed tomography apparatus according to the medical image diagnostic apparatus of the embodiment.

FIG. 11 is a flowchart showing an example of the procedures of blood flow inhibition index generation processing.

Volume data (perfusion volume data) regarding an organ of an object is read out from the storage unit 12 (step Sb1). The first region corresponding to a region dominated by a stenosed blood vessel and the second region corresponding to a region dominated by an unstenosed blood vessel are set in accordance with an operator instruction via the operation unit 13 (step Sb2). Based on the readout volume data (perfusion volume data), the first blood flow information in the first region and the second blood flow information in the second region are generated (step Sb3). Based on the first blood flow information and second blood flow information, blood flow inhibition indices in the stenosed blood vessel are generated (step Sb4). For both the first and second regions, the blood flow inhibition indices are displayed (step Sb5).

The above-described arrangement can yield the following effects.

In the X-ray computed tomography apparatus 4 according to the embodiment, the blood flow volume of a blood vessel is alternatively obtained from a tissue blood flow volume. The normal local blood flow volume $MBF_{normal}$ of the same myocardial portion when there is no stenosis is substituted by the local blood flow volume $K_{1remote}$ calculated from image information regarding a region dominated by an unstenosed blood vessel different from the stenosed blood vessel in the image. That is, a local blood flow volume used as the denominator is obtained not from a conventional normal value, but actually from volume data by CT perfusion, and is further obtained from a region dominated by an unstenosed blood vessel different from the stenosed blood vessel. This can suppress volume data-specific reliability degradation factors in regard to the generation of the blood flow inhibition index, and can improve the reliability.

Therefore, the X-ray computed tomography apparatus 4 according to the embodiment can obtain an index (blood flow inhibition index) equivalent to FFR from volume data (image data) without inserting a wire.

(Third Embodiment)

A medical image processing apparatus according to the third embodiment will be described below with reference to the accompanying drawings.

First, a "principle of obtaining an index equivalent to FFR from image data without inserting a wire" newly developed by the present inventors will be explained using the following numerical expressions. Note that the index equivalent to FFR is indicated by FFR' in order to discriminate it from FFR.

As represented by the following equation (1), FFR is given as a value obtained by normalizing, that is, dividing the blood flow volume of a stenosed blood vessel (stenosed blood vessel blood flow volume $Q_{stenosed}$) by the blood flow volume ($Q_{normal}$) of a blood vessel assumed not to be stenosed:

$$FFR \equiv Q_{stenosed}/Q_{normal} \qquad (1)$$

Figure 1:
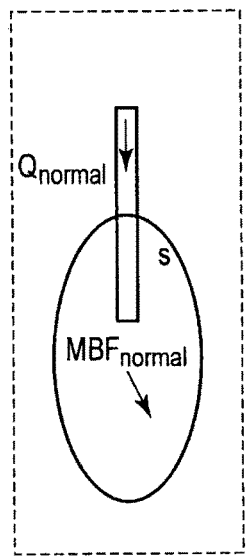
FIG. 1 is a view schematically showing the relationship between the pressure in a blood vessel and the normal local blood flow volume of a region dominated by the blood vessel according to an embodiment.

The pressure in a blood vessel is correlated with the blood flow volume at this portion. The blood flow volume of the blood vessel is equivalent in principle to the volume of a blood flowing through a tissue S (for example, part of the myocardium: to be simply referred to as a "myocardial portion" hereinafter) under the domination of this blood vessel (see FIG. 1). Letting MBF (Myocardial Blood Flow) be the local blood flow volume, equation (1) is rewritten into:

$$FFR \equiv Q_{stenosed}/Q_{normal} = \Sigma MBF_{stenosed}/\Sigma MBF_{normal} \qquad (2)$$

where $MBF_{stenosed}$ is the local blood flow volume of the myocardial portion suspected of ischemia under the domination of the stenosed blood vessel, and $\Sigma MBF_{stenosed}$ is the blood flow volume of the entire myocardial portion under the domination of the stenosed blood vessel. Similarly, $MBF_{normal}$ is the normal local blood flow volume of the same myocardial portion when there is no stenosis, and $\Sigma MBF_{normal}$ is the entire normal blood flow volume of the normal myocardial portion.

When S represents the volume of the myocardial portion, and $MBF_{stenosed}$ and $MBF_{normal}$ are replaced with the average values of local blood flow volumes in the respective regions for convenience, equation (2) can be rewritten into:

$$FFR \equiv Q_{stenosed}/Q_{normal} = \Sigma MBF_{stenosed}/\Sigma MBF_{normal} = \qquad (3)$$
$$(S \cdot MBF_{stenosed})/(S \cdot MBF_{normal}) = MBF_{stenosed}/MBF_{normal}$$

Here, when the average blood flow volume $MBF_{normal}$ of the myocardium on the assumption that there is no stenosis is considered to be equal to the average blood flow volume $MBF_{remote}$ of a blood vessel dominated by an actually unstenosed blood vessel, and is replaced by it, equation (3) can be rewritten into:

$$FFR \equiv Q_{stenosed}/Q_{normal} =$$
$$\Sigma MBF_{stenosed}/\Sigma MBF_{normal} = (S \cdot MBF_{stenosed})/(S \cdot MBF_{normal}) =$$
$$MBF_{stenosed}/MBF_{normal} = MBF_{stenosed}/MBF_{remote}$$

Let $K_1$ be the local blood flow volume calculated from image information, $K_{1stenosed}$ be the average value of the local blood flow volume of a stenosis-dominated region calculated from image information, and $K_{1remote}$ be the average value of a local blood flow volume calculated from image information in regard to a region dominated by an unstenosed blood vessel different from the stenosed blood vessel. Then, equation (3) can be rewritten into:

$$FFR' \equiv Q_{stenosed}/Q_{normal} = \qquad (4)$$
$$\Sigma MBF_{stenosed}/\Sigma MBF_{normal} = (S \cdot MBF_{stenosed})/(S \cdot MBF_{normal}) =$$
$$MBF_{stenosed}/MBF_{normal} = MBF_{stenosed}/MBF_{remote} =$$
$$(K_{1stenosed}/E_{stenosed})/(K_{1remote}/E_{remote})$$

where $E_{stenosed}$ and $E_{remote}$ are correction coefficients. For example, values of 0.5 and 0.6 are selected as $E_{stenosed}$ and $E_{remote}$.

Note that the correction coefficient E can be given by a relation: $E=(1-\exp(-PS/MBF))$ using PS as a predetermined coefficient for MBF. It is therefore possible to calculate MBF from only $K_1$ using the following equations (5) and (6), and calculate FFR' according to equation (3):

$$MBF_{stenosed} = K_{1stenosed}/(1-\exp(-PS/MBF_{stenosed})) \qquad (5)$$

$$MBF_{remote} = K_{1remote}/(1-\exp(-PS/MBF_{remote})) \qquad (6)$$

The important point here is as follows: as shown in FIG. 2, the blood flow volume of a blood vessel is alternatively obtained from a tissue blood flow volume. The normal local blood flow volume $MBF_{normal}$ of the same myocardial portion when there is no stenosis is substituted by the local blood flow volume $K_{1remote}$ calculated from image information regarding a region dominated by an unstenosed blood vessel different from a stenosed blood vessel in the image. That is, a local blood flow volume used as the denominator (modulus) is obtained not from a normal value as in equation (3), but actually from an image, and is further obtained from a region dominated by an unstenosed blood vessel different from the stenosed blood vessel. This can suppress image-specific reliability degradation factors of FFR' and can improve the reliability.

Figure 4:
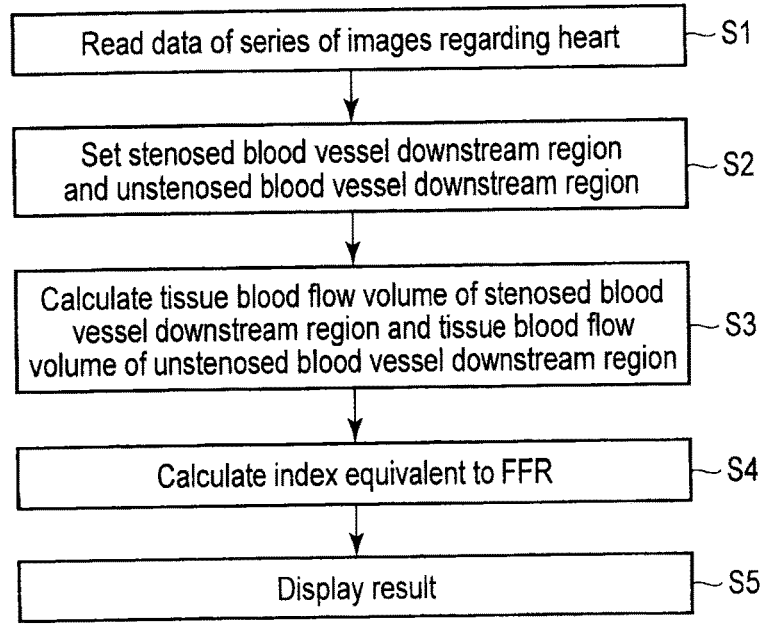
FIG. 4 is a flowchart showing procedures to calculate an index equivalent to FFR according to the embodiment.

FIG. 3 shows the arrangement of the medical image processing apparatus 10 according to the embodiment based on the above-described principle of obtaining an index equivalent to FFR from image data. FIG. 4 shows procedures to calculate the index (FFR') equivalent to FFR according to the embodiment. First, an image to be processed is generated by a modality capable of contrasting a blood flow by a tracer for the coronary artery of the heart serving as an imaging target and successively repetitively obtaining images, such as a SPECT apparatus 1, PET apparatus 2, CT apparatus 4, or X-ray apparatus 5. Data of a series of temporally successive images generated by any one of these modalities are loaded from the modality directly or from an external image server to the medical image processing apparatus 10 via an interface 11, and are stored in a storage unit 12 (S1).

Figure 5:
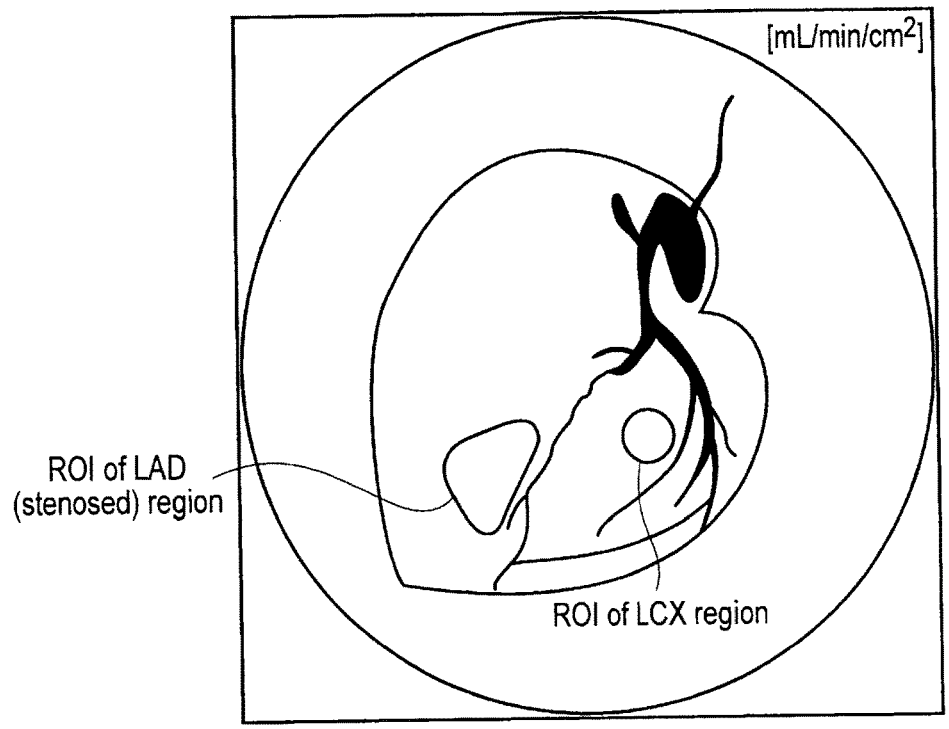
FIG. 5 is a view showing an example of region setting in FIG. 4.

As exemplified in FIG. 5, a user such as a doctor uses an operation unit 13 to specify a suspected stenosed portion on an image displayed on a display unit 14, and set, by ROI marks, a dominant region (to be referred to as a stenosed blood vessel downstream region) which receives supply of a blood from a blood vessel distributed downstream of the stenosed blood vessel, and a region (to be referred to as an unstenosed blood vessel downstream region) dominated by an unstenosed blood vessel branched from the stenosed blood vessel (S2). Note that the relationship between the portion of each blood vessel (coronary artery) in the heart and a dominant region positioned downstream of it is generally defined. Hence, when the user designates portions on blood vessels, the stenosed blood vessel downstream region and unstenosed blood vessel downstream region (dominant regions) may be automatically set.

As shown in FIG. 2, a tissue blood flow calculation unit 15 obtains blood flow volumes (local blood flow volumes) at a plurality of local portions in the stenosed blood vessel downstream region, and similarly obtains local blood flow volumes in the unstenosed blood vessel downstream region (S3). Then, the tissue blood flow calculation unit 15 calculates the average values of the local blood flow volumes in the respective regions. The average value of the local blood flow volumes will be simply referred to as a local blood flow volume.

The local blood flow volume calculation method is as follows. A so-called mask image in which the contrast medium does not flow is subtracted from a series of images during a period till the completion of outflow of a contrast medium after the start of inflow. The difference images represent a stain distribution (contrast medium concentration distribution) by the contrast medium. The pixel values of the difference images reflect contrast medium concentrations. A plurality of local portions are set in a lattice in the stenosed blood vessel downstream region. An average pixel value is calculated for each local portion from each difference image for the series of difference images. Then, a time-to-density curve is generated. A local blood flow volume $K_{1stenosed}$ is obtained from the time-to-density curve by using a model analysis-based theory (patent literature 1 (Jpn. Pat. Appln. KOKAI Publication No. 2008-136800)). As for the unstenosed blood vessel downstream region, a local blood flow volume $K_{1remote}$ is similarly calculated.

An index calculation unit 16 calculates FFR' according to equation (4) from the obtained local blood flow volume $K_{1stenosed}$ in the stenosed blood vessel downstream region and local blood flow volume $K_{1remote}$ in the unstenosed blood vessel downstream region (S4). The display unit 14 displays the calculated FFR' (S5). It is also possible to obtain $MBF_{stenosed}$ and $MBF_{normal}$ from the above-described equations (5) and (6) without using the correction coefficients $E_{stenosed}$ and $E_{remote}$, and calculate FFR'=$MBF_{stenosed}$/$MBF_{normal}$ from equation (3).

In this manner, according to the embodiment, an index equivalent to FFR can be obtained from image data without inserting a wire.

The blood flow inhibition index generation function according to the embodiments and modification can also be implemented by installing, in a computer such as a work station, a program (blood flow inhibition index generation program) for executing blood flow inhibition index generation processing, and expanding it on a memory. At this time, a program capable of causing the computer to execute this method can also be distributed by storing it in a storage medium such as a magnetic disk (e.g., Floppy® disk or hard disk), an optical disk (e.g., CD-ROM or DVD), or a semiconductor memory.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus, comprising:
a memory to store (1) volume data or data of a series of images regarding an organ of an object, (2) a first extraction value of a first blood flow volume entering a first tissue region from a first blood vessel, the first tissue region dominated by the first blood vessel located downstream of a stenosed portion in the volume data or the data of the series of images, and (3) a second extraction value of a second blood flow volume entering a second tissue region from a second blood vessel, the second tissue region dominated by the second blood vessel, which is an unstenosed blood vessel in the volume data or the data of the series of images;
processing circuitry configured to
generate, using density of a pixel value caused by a contrast medium in the first tissue region, the first blood flow volume;
generate, using density of a pixel value caused by the contrast medium in the second tissue region, the second blood flow volume;
calculate a first value by dividing the first blood flow volume by the first extraction value;
calculate a second value by dividing the second blood flow volume by the second extraction value; and
generate, by dividing the first value by the second value, a blood flow inhibition index representing a degree of inhibition of a vascular blood flow regarding the first tissue region; and
a display to display the blood flow inhibition index together with the first tissue region and the second tissue region.

2. The medical image diagnostic apparatus according to claim 1, wherein the processing circuitry is further configured to
generate, based on the volume data or the data of the series of images, a third blood flow volume corresponding to respective pixels in a region different from the first tissue region and the second tissue region in a display region displayed by the display,
generate an additional blood flow inhibition index corresponding to the respective pixels based on the third tissue blood flow volume corresponding to the respective pixels and the second blood flow volume, and
cause the display to display the additional blood flow inhibition index in a predetermined hue corresponding to a value of the additional blood flow inhibition index for the respective pixels.

3. The medical image diagnostic apparatus according to claim 1, wherein the organ includes a heart of the object, and the blood flow inhibition index includes an index equivalent to a fractional flow reserve.

4. The medical image diagnostic apparatus according to claim 3, wherein the first blood flow volume and the second blood flow volume correspond to a specific cardiac phase of the heart or are average blood flow volumes of all cardiac phases.

5. The medical image diagnostic apparatus according to claim 1, wherein the volume data includes data regarding nuclear medicine tomography or X ray computed tomography, and
the data of the series of images include data regarding X ray diagnostic imaging.

6. The medical image diagnostic apparatus according to claim 1, wherein the processing circuitry is further configured to set the first tissue region and the second tissue region on an image displayed on the display based on an operator instruction.

7. A medical image processing method, comprising:
storing (1) volume data or data of a series of images regarding an organ of an object, (2) a first extraction value of a first blood flow volume entering a first tissue region from a first blood vessel, the first tissue region dominated by the first blood vessel located downstream of a stenosed portion in the volume data or the data of the series of images, and (3) a second extraction value of a second blood flow volume entering a second tissue region from a second blood vessel, the second tissue region dominated by the second blood vessel, which is an unstenosed blood vessel in the volume data or the data of the series of images;

generating, using density of a pixel value caused by a contrast medium in the first tissue region, the first blood flow volume;

generating, using density of a pixel value caused by the contrast medium in the second tissue region, the second blood flow volume;

calculating a first value by dividing the first blood flow volume by the first extraction value;

calculating a second value by dividing the second blood flow volume by the second extraction value;

generating, by dividing the first value by the second value, a blood flow inhibition index representing a degree of inhibition of a vascular blood flow regarding the first tissue region; and displaying, on a display, the blood flow inhibition index together with the first tissue region and the second tissue region.

* * * * *